United States Patent
Noel

(10) Patent No.: US 8,222,379 B2
(45) Date of Patent: Jul. 17, 2012

(54) METHOD OF SEPARATION BY ADSORPTION

(75) Inventor: Robert John Noel, Saltburn (GB)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 10/521,730

(22) PCT Filed: Sep. 5, 2003

(86) PCT No.: PCT/GB03/03953
§ 371 (c)(1),
(2), (4) Date: Jan. 20, 2005

(87) PCT Pub. No.: WO2004/022196
PCT Pub. Date: Mar. 18, 2004

(65) Prior Publication Data
US 2005/0245729 A1    Nov. 3, 2005

(30) Foreign Application Priority Data

Sep. 9, 2002 (GB) .................................. 0220894.0

(51) Int. Cl.
*C07K 1/18* (2006.01)
(52) U.S. Cl. .................. 530/416; 530/390.1; 530/413
(58) Field of Classification Search .................. None
See application file for complete search history.

(56) References Cited

U.S. PATENT DOCUMENTS

| | | | |
|---|---|---|---|
| 4,883,598 A * | 11/1989 | Riethorst et al. | 210/656 |
| 5,147,536 A * | 9/1992 | Engstrom | 210/198.2 |
| 5,174,536 A | 12/1992 | Pelletier et al. | |
| 5,429,746 A * | 7/1995 | Shadle et al. | 210/635 |
| 5,644,036 A * | 7/1997 | Ramage et al. | 530/412 |
| 5,945,520 A * | 8/1999 | Burton et al. | 536/20 |
| 5,986,063 A | 11/1999 | Etzel | 530/366 |
| 6,498,236 B1 * | 12/2002 | Lihme et al. | 530/387.1 |
| 7,214,321 B2 * | 5/2007 | Belew et al. | 210/660 |
| 2005/0020812 A1 * | 1/2005 | Angus | 530/333 |
| 2006/0194953 A1 * | 8/2006 | Bonnerjea et al. | 530/387.1 |

FOREIGN PATENT DOCUMENTS

| WO | 97/26797 A1 | 7/1997 |
|---|---|---|
| WO | WO 98/08603 | * 3/1998 |

OTHER PUBLICATIONS

Wu et al, Jour. Chromat., 598, 7-13, 1992.*
Graf et al, Bioseparation, vol. 4, 7-20, 1994.*
Hahn et al, Journal or Chromatography A, vol. 795, 277-287, 1998.*
Dephillips, P. et al., Determinants of Protein Retention Characteristics on Cation-Exchange Adsorbents, J. Chromatography A, 933(1-2):57-72, Nov. 9, 2001.
Scholz, G.H. et al., Salt-independent Binding of Antibodies from Human Serum to Thiophilic Heterocyclic Ligands, J. Chromatography B: Biomedical Sciences & Applications, 709:189-196, 1998.
Burton, S.C. et al., "Hydrophobic Charge Induction Chromatography: Salt Independent Protein Adsorption and Facile Elution with Aqueous Buggers" J. Chromatography A, 814(1-2):71-81, Jul. 24, 1998.
International Search Report, Dec. 16, 2003.
Chang et al., "Comparison of protein adsorption isotherms and uptake rates in preparative cation-exchange materials", Journal of Chromatography A. vol. 827, No. 2. Dec. 11, 1998, pp. 281-293.
International Preliminary Examination Report received for PCT Patent Application No. PCT/GB2003/003953, completed on Mar. 4, 2004, 2 pages.

* cited by examiner

*Primary Examiner* — David A Saunders
(74) *Attorney, Agent, or Firm* — EMD Millipore Corporation

(57) ABSTRACT

A method of separating a selected ionic component from a sample, comprises contacting the sample with an ionic adsorbent whose charge density is such that the component is bound selectively in the absence of added ionic component that competitively binds the adsorbent.

9 Claims, 2 Drawing Sheets

METHOD OF SEPARATION BY ADSORPTION

CROSS REFERENCE TO RELATED APPLICATIONS

This application is the U.S. National Stage Application of International Application No.: PCT/GB2003/003953, filed on Sep. 5, 2003, which claims priority to GB Application No.: 0220894.0, filed on Sep. 9, 2002.

FIELD OF THE INVENTION

The present invention relates to a method of separation by adsorption.

BACKGROUND OF THE INVENTION

Under certain conditions, adsorbent materials containing ionic groups can bind molecules of a net opposing charge. Such processes, for example chromatography, are currently utilised in the purification and separation of biomolecules in a complex mixture such as blood or fermentation or cell culture broths.

In column chromatography, the mixture to be analysed is applied to the top of a column comprising an adsorbent material which acts as the "stationary phase". A liquid solvent (the "mobile phase") is passed through the column under gravity or pressure carrying the dissolved mixture. Because the different compounds in the mixture have different ionic interactions with the mobile and stationary phases, they will be carried along in the mobile phase to varying degrees, resulting in separation. A salt gradient is then usually applied to remove, in turn, separate bound components.

In such processes, the exact conditions for separation are typically determined by trial and error. The operational selectivity of an adsorbent relates to the number of molecules that bind to it as the mixture passes over; under normal conditions there is generally low specificity. Variation in the pH or ionic strength causes the interaction between individual components of the mixture and adsorbent to change. The ionic strength may be varied to allow a desired component to adsorb, but so that solvent molecules or additional components compete for available binding sites on the adsorbent, thus preventing the binding of an undesired component. Selectivity also varies depending on the physical structure of the adsorbent, for example the size distribution of pores or the chemical nature of the underivatised adsorbent.

The "working capacity" (dynamic capacity) of an adsorbent refers to the amount of a particular component which will bind to and be retained on the adsorbent. Working capacity is dependent on, inter alia, the charge density, ligand type and pore size distribution of the adsorbent.

Chang et al [Journal of Chromatography A, 827 (1998), 281-293] suggests that the protein adsorption capacity of an adsorbent is strongly correlated with the accessible surface area, and less so with the intrinsic adsorption affinity. The authors propose that uptake dynamics are influenced to a large extent by mean pore size, although it is acknowledged that other structural parameters, such as pore connectivity and adsorption affinity, may also play a role.

DePhillips et al [Journal of Chromatography A, 933 (2001), 57-72] reports that, above a threshold amount, increased charge density and ionic capacity do not necessarily result in increased protein retention. DePhillips et al postulate that a high charge density is relatively unimportant, proposing that an equivalent capacity may be attained by optimally orientating and positioning ligands of lower charge density. The data presented are based on experiments using additional salt to optimise the ionic strength.

In summary, research in this field has, over time, suggested that an increase in the charge density of the adsorbent leads, up to a point, to an, increased capacity, when added competing salts are used.

Analytical and production-scale chromatography differ, inter alia, in the way in which their performance is measured. For analytical separations, the overriding requirement is that analysis is rapid; this is often achieved using small, non-porous stationary phase particles. For large-scale chromatographic processes, capacity, recovery and throughput are typically the factors on which performance is judged. Optimum performance may be achieved by trading off throughput against selectivity and recovery. Currently, desirable working capacity is attained by using adsorbents of high charge density, with additional salt or buffer incorporated in the mobile phase. As mentioned above, the presence of additional salt (e.g. NaCl) reduces the strength of interaction between the stationary and mobile phase, allowing the specific binding of a particular component.

Current methodologies suffer from a number of limitations, one of which is cost. A major factor in the manufacture of biomolecules is the cost of raw materials. Buffered solutions are required to stabilise biomolecules against variations in pH and to reduce the likelihood of insolubilisation (precipitation). For this reason, concentrations of buffer/salt components are kept to a minimum in feed solutions and usually range from 10 to 100 mM, depending on the biomolecule to be stabilised.

SUMMARY OF THE INVENTION

The present invention is based on the realisation that, rather than using the combination of a high charge density adsorbent and added salt in the sample, desirable working capacity may be attained by varying the charge density of binding surfaces of the adsorbent. For example, while DePhillips et al reports that increased charge density and ionic capacity do not necessarily result in increased protein retention, this publication does not, on the basis of the data presented, systematically address charge density as a retention variable.

According to the invention, a method of separating a selected ionic component from a sample, comprises contacting the sample with an ionic adsorbent whose charge density is such that the component is bound selectively, in the absence of an added ionic component that competitively binds the adsorbent. The charge density of the adsorbent is preferably 10 to 100 μmol/ml, more preferably 20 to 90 μmol/ml, and most preferably 30 to 80 μmol/ml. In a preferred embodiment, the adsorbent material is cationic, the material preferably comprising sulphopropyl groups supported on a suitable substrate, for example agarose or Sepharose.

The invention utilises the finding that the charge density may be low enough to allow binding with only one ionic component, the interaction with other components being too weak for them to bind. In this way, high selectivity and capacity may be achieved at relatively low cost, since the use of large quantities of additional salts is no longer necessary.

By optimising the charge density of the adsorbent surface, the invention provides a highly selective method of separation. A method of the invention involves a marked reduction in the amount of adsorbent-bound competing molecules, allowing greater working capacities to be attained within typical ranges of pH and ionic strength.

The invention bypasses the need for the inclusion of competing ionic. components (e.g. salts) in the sample. Selectivity is achieved by using an adsorbent of predetermined charge density suitable for selective binding of the ionic component of interest over a range of ionic strengths. Thus a sample may be brought directly into contact with the adsorbent, without any pretreatment.

DESCRIPTION OF PREFERRED EMBODIMENTS

The present invention may be used for the separation of ionic polymeric compounds. In particular, the present invention may be used for the separation of biomolecules such as those found in complex mixtures such as blood and cell culture broths. A method of the invention may be used in the production of a monoclonal or polyclonal antibody, since antibody production generally requires a protein-specific purification step, such as protein A purification.

The adsorbent used in a method of this invention is an optionally derivatised solid phase or insoluble compound which is capable of ionic interaction with the liquid phase. The adsorbent may comprise a ceramic, synthetic or natural polymeric material, or a mixture thereof. For example, the adsorbent may comprise dextran or another natural polymer chemically or physically attached to a solid phase.

Selection of an adsorbent of appropriate charge density can be achieved using any suitable method or technique known in the art. The exact value will depend on factors known to those of ordinary skill in the art. One factor is the nature of the material to be bound and/or that which should not be bound. Another is the nature of the charged entities on the adsorbent, of which a variety can be used.

Selectivity may be achieved by using an adsorbent of sufficiently low ionic charge density such that only the component of interest binds to it. An example of this is the separation of a mixture of immunoglobulin (IgG) and protein A. Sulphopropyl groups having an (cat)ionic strength of >140 µmol/ml bind both proteins and the IgG-protein A complex. Sulphopropyl groups having weaker charge density, of approximately 75 µmol/ml, are selective towards IgG, the result being that, after elution, protein A is observed in the unbound fraction and IgG in the bound fraction.

Separation may be carried out using any suitable apparatus known in the art, for example an ion-exchange column. Elution may also be conducted by known procedures.

Techniques such as polyacrylamide gel electrophoresis (PAGE), in particular sodium dodecyl sulphate (SDS-PAGE), may be used to analyse the various fractions of separation.

The following Examples illustrate the invention, with reference to the accompanying drawings, in which.

EXAMPLE 1

Separation of Immunoglobulin and Protein A

Agarose beads were manufactured, cross-linked and chemically derivatised with sulphopropyl (SP) groups of varying charge densities. For comparison, a commercially available SP adsorbent, SP Sepharose, was also used.

Immunoglobulin G and protein A were mixed in the ratio 10:1 (w/w) in a buffered solution, pH 4.0-5.5 and conductivity 2-6 mSi/cm. Three different SP-based cation-exchange adsorbents were analysed for selectivity of binding. These contained 75 µmol/ml SP agarose cationic groups, 140 µmol/ml SP agarose cationic group and SP sepharose containing 200-250 µmol/ml cationic groups.

One column volume of the protein mixture was applied to a packed column of buffer-equilibrated SP adsorbent at a flow rate of 100 to 300 cm/hr. The column was then washed with buffered solution to remove non-bound protein, and a salt gradient of increasing conductivity was applied to the column in order to elute ionically-bound proteins.

The eluent from the column was analysed for absorbance at 220 nm using an on-line detector. A variety of pH and conductivity values was utilised within the ranges defined above. Non-bound fractions and bound-eluted fractions were retained from each column run, and analysed for protein content using SDS-PAGE.

Figure 1:
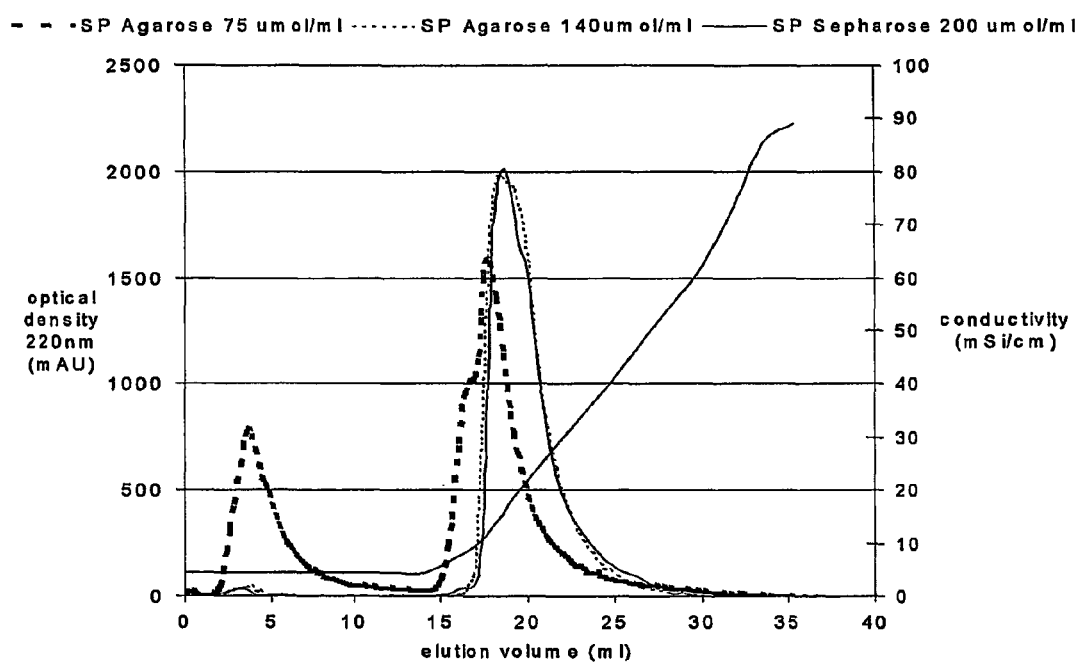
FIG. 1 is a graph showing the elution profiles of three adsorbents of different charge density used in the separation of IgG and protein A.

The results are shown in FIG. 1. The SP adsorbents with >140 µmol/ml cationic groups bound all the protein components; IgG, protein A and the complex between IgG and protein. However, the adsorbent with only 75 µmol/ml (dashed line) shows a substantial quantity of protein in the unbound fraction; this non-binding protein fraction was shown to be approximately 90% protein A and 10% IgG. The eluting protein fraction was shown to contain 98% IgG and 2% protein A. It is evident that the cationic adsorbent with lower charge density has not bound protein A.

EXAMPLE 2

Separation of Acidic Cheese Whey Proteins

Cheese whey was obtained from de-fatted milk and the pH adjusted to 4.3 with dilute phosphoric acid. One column volume of the protein mixture was applied to the three SP cationic adsorbents described in Example 1, in order to separate the different proteins. The proteins were washed from the column with a buffer solution of pH 4.3. The proteins were eluted from each adsorbent column using a gradient of increasing sodium chloride concentration (0 to 1M). The salt gradient was applied along each adsorbent column at an elution volume range of 12 to 50 ml. The eluent from each column was analysed for absorbance at 280 nm using an on-line detector.

Figure 2:
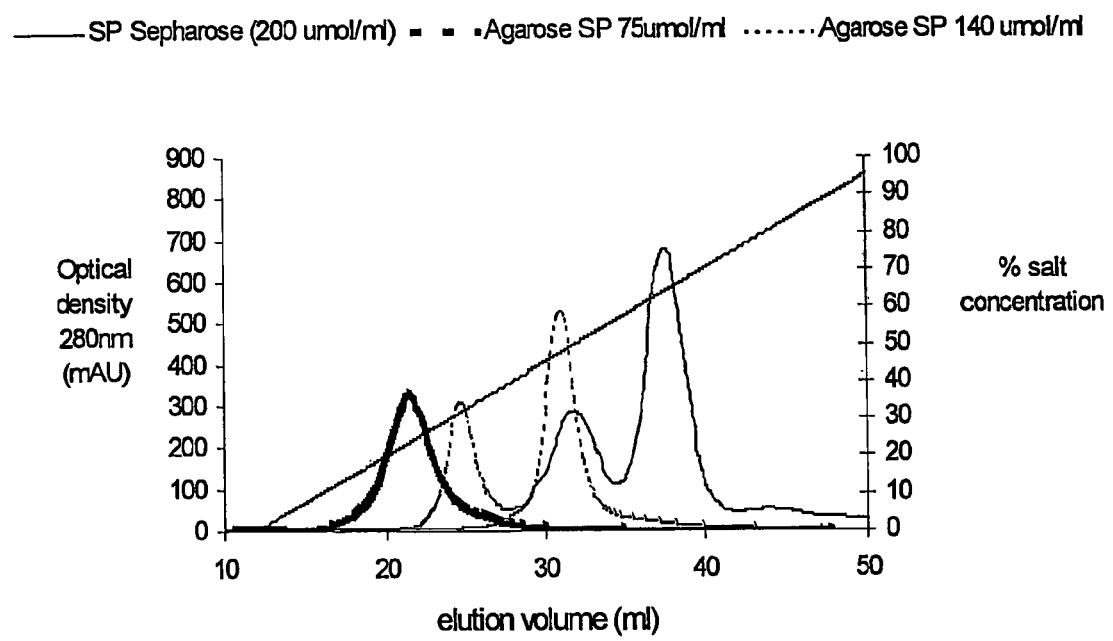
FIG. 2 is similar to FIG. 1, except that the elution profiles pertain to the separation of acidic cheese whey proteins.

FIG. 2 shows three elution profiles (optical density at 280 nm versus elution volume) conducted using the three different cation adsorbents under the same binding and elution gradient conditions. The three cationic adsorbents had different ionic charge densities. The optical density traces show how the acidic whey proteins were bound and eluted from each adsorbent.

The absorbance profiles show two proteins separated into distinct peaks for the adsorbents having >100 µmol/ml ionic charge density. The adsorbent with <100 µmol/ml ionic charge density was more selective, binding and eluting only one protein.

The invention claimed is:

1. A method of separating immunoglobulin G, an ionic protein compound of interest, from a protein sample comprising protein A using a selective cation-exchange adsorbent having a sufficiently low ionic charge density to ionically bind to immunoglobulin G consisting essentially of the following steps;

(a) contacting a protein sample having a conductivity between 2-6 mSi/cm and containing immunoglobulin G and protein A, with a selective cation-exchange adsorbent consisting of agarose beads having sulphopropyl groups attached thereto and having an ionic charge density from 10 to 100 µmol/ml;

(b) ionically binding the immunoglobulin G to the agarose beads having sulphopropyl groups attached thereto, (c) washing the agarose beads having sulphopropyl groups attached thereto with a buffered solution to remove unbound protein A,
(d) applying a salt gradient of increasing conductivity to the agarose beads having sulphopropyl groups attached thereto, and
(e) eluting the ionically bound immunoglobulin G from the agarose beads having sulphopropyl groups attached thereto.

2. The method according to claim 1, wherein the selective cation-exchange adsorbent has an ionic charge density from 20 to 90 μmol/ml.

3. The method according to claim 1, wherein the selective cation-exchange adsorbent has an ionic charge density from 30 to 80 μmol/ml.

4. The method according to claim 1, wherein the pH of protein sample solution is 4.0-5.5.

5. A method of separating protein A from immunoglobulin G in a buffered protein sample solution having a pH 4:0-5.5 using a selective cation-exchange adsorbent having sulphopropyl groups, consisting essentially of the following steps:
(a) contacting the buffered protein sample solution having a pH 4.0-5.5 and a conductivity 2-6 mSi/cm, protein A and immunoglobulin G with a selective cation-exchange adsorbent having sulphopropyl groups attached thereto and an ionic charge density from 10 to 100 μmol/ml to ionically bind to the immunoglobulin G, and
(b) washing the selective cation-exchange adsorbent with a buffered solution to remove unbound protein A.

6. The method according to claim 5, which further comprises
(c) applying a salt gradient of increasing conductivity to the selective cation-exchange adsorbent, and eluting the bound immunoglobulin G from the selective cation-exchange adsorbent.

7. The method according to claim 5, wherein the selective cation-exchange adsorbent has an ionic charge density from 20 to 90 μmol/ml.

8. The method according to claim 5, wherein the selective cation-exchange adsorbent has an ionic charge density from 30 to 80 μmol/ml.

9. The method according to claim 5, wherein the selective cation-exchange adsorbent comprises agarose beads.

* * * * *